US00PP09224P

United States Patent [19]

Ison

[11] Patent Number: Plant 9,224

[45] Date of Patent: Aug. 1, 1995

[54] 'LATE FRY' MUSCADINE GRAPE

[76] Inventor: William G. Ison, Box 190, Brooks, Ga. 30205

[21] Appl. No.: 241,726

[22] Filed: May 12, 1994

[51] Int. Cl.[6] ..... A01H 5/00

[52] U.S. Cl. ..... Plt./47.2

[58] Field of Search ..... Plt. 47.2

[56] References Cited

U.S. PATENT DOCUMENTS

P.P. 5,823 12/1986 Ison ..... Plt./47.2

*Primary Examiner*—James R. Feyrer

*Attorney, Agent, or Firm*—James A. Hinkle

[57] ABSTRACT

A cross between the female variety Fry and the pollen parent variety Granny Val to produce an improved variety of muscadine grape.

2 Drawing Sheets

DESCRIPTION OF THE VARIETY

A cross between the female variety Fry and the pollen parent variety Granny Val, U.S. Plant Pat. No. 5,823.

The primary objective of the breeding was to produce an improved variety of muscadine plant that has fruit which ripens later than other muscadine grapes and extends the season of muscadine production by one or two weeks. The fruit is large, sweet, bronze, and dry scar. The grape vine of the invention is self-fertile, and produces late season fruit having characteristics superior to those of either parent variety. These characteristics include the plant having approximately eighty to ninety percent even ripening fruit with high acid, and the plant being vigorous and productive.

In comparison with the pollen parent, the fruit of the new variety is slightly larger and more dry stem scar. The vine of the new variety requires less pruning than the pollen parent as the pollen parent produces excess fruit and must be pruned more to balance the vigor with the fruit. In comparison with the seed parent, the fruit of the new variety is larger, sweeter, more dry stem scar, more even ripening, and later ripening. Due to the plant's characteristics of even ripening, the new variety can be mechanically harvested with one picking. Late Fry can be completely hand harvested with two pickings. The present variety yields on the average of from five to eight tons per acre in tests conducted at Ison's Nursery & Vineyards, Brooks, Ga. This variety is outstanding for fresh fruit due to its excellent flavor.

Asexual reproduction of the new variety either by soft wood cuttings or by layering as performed at Brooks, Ga., shows that the above characteristics and distinctions come true to form and are established and transmitted through succeeding propagations.

BRIEF DESCRIPTION OF THE VIEWS OF THE DRAWING

The accompanying drawing shows various portions of specimens of the new variety in three views wherein:

The top photograph of the first sheet is a close-up of a typical cluster of berries, at a mature ripe stage, of the new plant showing the shape and color of the fruit and the surface characteristics of the fruit, canes and tendrils;

The bottom photograph of the first sheet shows a typical vine of the new variety 'Late Fry' trained to a single wire, vertical trellis method with one horizontal branch extending along the wire in opposite directions from the main stem; and, The photograph of the second sheet depicts two leaves of typical shape taken from a specimen of 'Late Fry', taken with a tape measure to give an indication of leaf size, the leaf on the left showing the top surface, coloration, shape, margin characteristics and venation; and, the photograph on the left showing the leaf bottom characteristics of a typical leaf of the new plant.

The color is nearly as true as is reasonably possible to make the same in photographic illustrations of this type.

DETAILED BOTANICAL DESCRIPTIONS OF THE PLANT

The following is a detailed description of the new variety:

Species: *Vitis Rotundifolia.*

Type: Vine.

Seed parent: Fry.

Pollen parent: Granny Val, U.S. Plant Pat. No. 5,823.

Propagation: Holds its characteristics through succeeding propagation by either layering or by soft wood cuttings.

Locality where grown: Brooks, Ga.

Fruit:

*Borne.*—Usually in clusters of four to ten berries. This new variety ripens between October 15th and November 5th in Brooks, Ga. The seed parent Fry ripens between September 1st and October 1st in Brooks, Ga., and the pollen parent Granny Val ripens between October 8th and October 20th in Brooks, Ga.

*Fruit size.*—$1\frac{1}{8}$ to $1\frac{1}{4}$ diameter, similar in size to the pollen parent Granny Val. The lenticels on the skin of the fruit are medium in size relative to the average.

*Color.*—Greyed Orange, 163D Fan 4 Royal Horticultural Society, London England.

*Sugar content.*—The new variety has a 20% solid soluble average. The seed parent Fry has a 18–19% solid soluble average, and the pollen parent Granny Val has a 21.5 to 22.5 percent solid soluble average.

*Acidity.*—On the 1–14 scale for ph with 7 being neutral, the free-run juice of the seed parent Fry has a ph of 3.4, the free-run juice of the pollen parent Granny Val has a ph of 3.1, and the free-run juice of the new variety has a ph of 2.9.

*Taste.*—The seed parent Fry is the industry standard muscadine for quality. On a scale of 1–5 for taste with 5 being the best, the Fry rated 5, the Granny Val rated 2 and the Late Fry rated 4.7. The new variety Late Fry has a sweet, tender pulp and thin, non-edible skin. The Late Fry has an excellent overall flavor with no undesirable aftertaste and has a good sugar-acid balance which makes it excellent for fresh eating. Because of the blend of sugar and acid content, the Late Fry is much superior to the Granny Val. These findings are based on taste panel determinations conducted at Ison's Nursery and at the Experiment Station in Tifton, Ga.

*Shape.*—Round.

*Seed.*—The seeds of the new variety are approximately ¼" long and 3/16" wide and have no transverse ridges. On the average, there are approximately 2.7 seeds per berry.

*Pulp.*—Color Group Fan 4, 195B, Royal Horticultural Society, London, England. The consistency is medium soft compared to most muscadine varieties.

*Skin.*—Medium thickness.

Foliage: The leaves are approximately 3 inches long and 3.5 inches wide and glabrous on the top and bottom. The leaves are circular, prelobed, and have an open petiole sines. The top of the leaf is Color Group Fan 3, 137A of The Royal Horticultural Society, London, England, and the bottom of the leaf is Color Group Fan 3, 138b of The Royal Horticultural Society, London, England. The leaf margins are broadly toothed. The stems of the leaves are 1.75" to 3.25" in length with a thickness of approximately 1/16". The coloration of the leaf stem is Color Group Fan 3, 153A of The Royal Horticultural Society, London, England. The mature bark is smooth, narrow, and elliptic, and the main canes are grayish brown in color.

Reproductive organs: Self-fertile. The average-blooming dates for the plant are May 15th to June 18th compared to other plants which bloom between May 20th and June 10th. This plant will expand the potential range for culture in the southern range of where it is grown.

Canes: Medium to large calipers. The canes are semi-drooping and normally grow 3 to 4 feet in length. The color of the canes is Grey Green, 198B of The Royal Horticultural Society, London, England. The variety typically produces 9 canes per foot of cordon, and the top growth of canes produced per year is 4 feet. The cane thickness is 3/16" to ½", and the range of internode length is 1 to 2¾". The tendrils are simple and intermittent.

Diseases: Tolerant to block rot and ripe rot, and disease resistant.

Growth habits: The plant requires support and is vigorous and productive. On a scale of one to five with five indicating the most vigorous, the Granny Val, Fry and the new variety Late Fray rate 1, 3, and 5 respectively. In productivity the pollen parent Granny Val produces approximately eighty pounds per vine, the seed parent Frey produces approximately fifty pounds per vine, and the new variety produces approximately fifty six pounds per vine in tests at Brooks, Ga.

Pruning and training: The vines for the new variety as well as for the parent plants are trained with the single wire, vertical trellis method but they could be trained with the Geneva double curtain method. The vines are pruned back to three buds for controlling the growth. Agricultural ties and the tendrils hold the vine to the wire. On a scale of one to five with five indicating the most pruning required, the Fry and Late Fry rate 1 and 2 respectively. The new variety Late Fry requires more pruning than the seed parent Fry due to its greater vigor. On the same scale for pruning requirements, the pollen parent Granny Val rates 3 due to excessive fruiting. The mature vine of the new variety averages 4" in diameter at the base.

This description was made from a muscadine vine grown at Ison's Nursery & Vineyards, Brooks, Ga.

I claim:

1. The new and distinct variety of grape plant as described and illustrated.

* * * * *

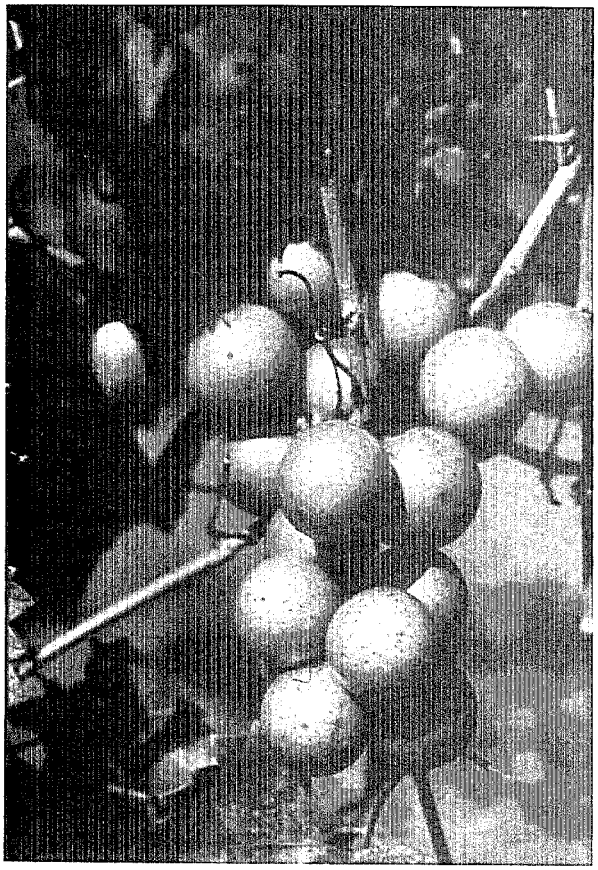
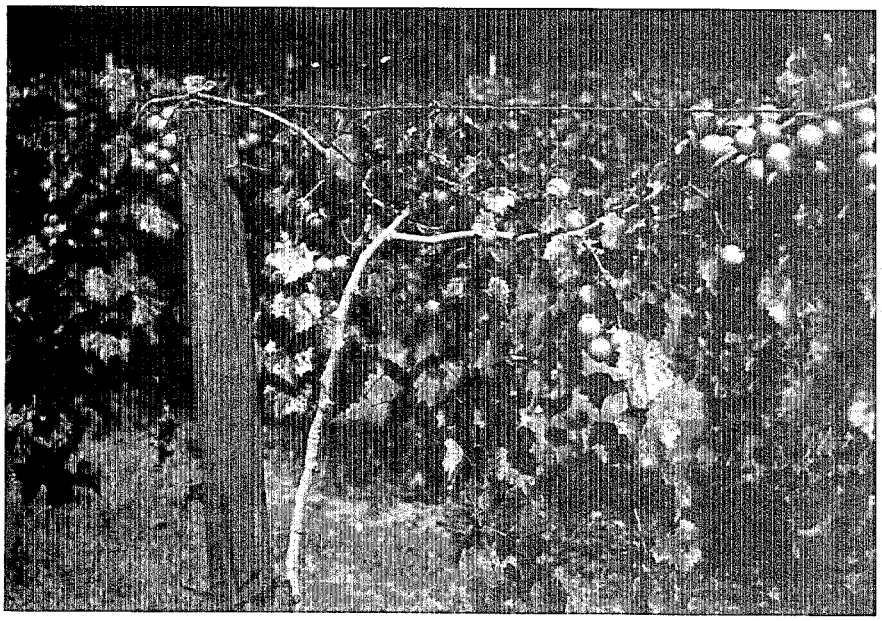

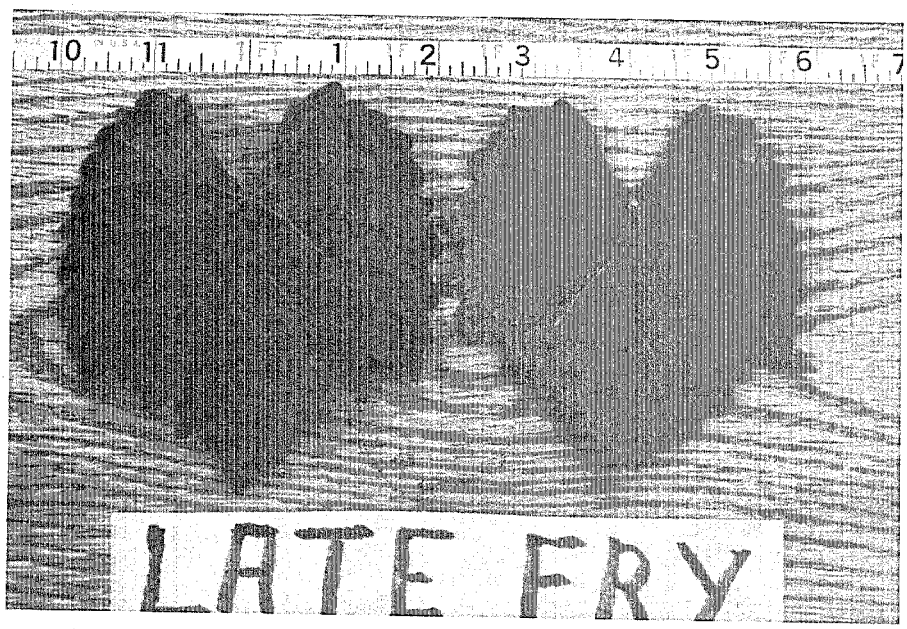
10
11
1
2
3
4
5
6
LATE FRY